United States Patent [19]

Hengartner et al.

[11] 4,360,521
[45] Nov. 23, 1982

[54] 7[3,6-DIHYDRO-1(2H)-PYRIDYL]-2-OXO-2H-[1,2,4]OXADIAZOLO[2,3-C]PYRIMIDINE-5-CARBAMATE COMPOUNDS

[75] Inventors: Urs Hengartner, Basel, Switzerland; Jean-Claude Muller, Rixheim, France; Henri Ramuz, Birsfelden, Switzerland

[73] Assignee: Hoffmann-La Roche Inc., Nutley, N.J.

[21] Appl. No.: 327,384

[22] Filed: Dec. 4, 1982

[30] Foreign Application Priority Data

Dec. 19, 1980 [CH] Switzerland .................. 9410/80
Oct. 2, 1981 [CH] Switzerland .................. 6350/81

[51] Int. Cl.³ .................. C07D 498/22; A61K 31/505
[52] U.S. Cl. .................. 424/251; 544/255; 544/323; 544/324; 548/262; 548/325; 548/335
[58] Field of Search .................. 544/255; 424/251

[56] References Cited

U.S. PATENT DOCUMENTS

| | | | |
|---|---|---|---|
| 4,150,131 | 4/1979 | Muller et al. | 424/251 |
| 4,150,132 | 4/1979 | Muller et al. | 424/251 |
| 4,220,772 | 9/1980 | Muller et al. | 424/251 |
| 4,276,417 | 6/1981 | Muller et al. | 544/198 |

*Primary Examiner*—Donald G. Daus
*Assistant Examiner*—Sharon A. Gibson

*Attorney, Agent, or Firm*—Jon S. Saxe; Bernard S. Leon; William G. Isgro

[57] ABSTRACT

Oxadiazolo[2,3-c]pyrimidine derivatives of the formula

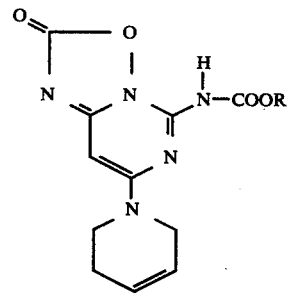

wherein R is alkyl, alkenyl, alkynyl or alkoxyalkyl, as well as their salts, are described. The compounds of formula I have valuable, long-lasting vasodilating and/or blood pressure-lowering properties and are useful for the treatment of vascular-conditioned hypertensions or as vasodilators in peripheral blood supply disorders. The compounds are prepared, inter alia, by carbamoylating the corresponding derivative containing a free amino group and optional salt formation.

12 Claims, No Drawings

7[3,6-DIHYDRO-1(2H)-PYRIDYL]-2-OXO-2H-[1,2,4]OXADIAZOLO[2,3-C]PYRIMIDINE-5-CARBAMATE COMPOUNDS

BRIEF SUMMARY OF THE INVENTION

The invention relates to oxadiazolo[2,3-c]pyrimidine derivatives of the formula

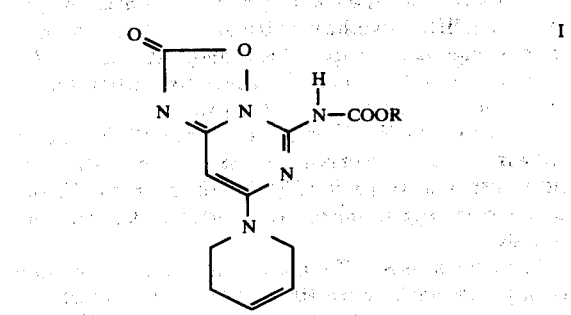

wherein R is alkyl, alkenyl, alkynyl or alkoxyalkyl, as well as their pharmaceutically acceptable salts.

In another aspect, the invention relates to 5-amino-7-[3,6-dihydro-1(2H)-pyridyl]-2H-[1,2,4]-oxadiazolo[2,3-c]pyrimidin-2-one of the formula

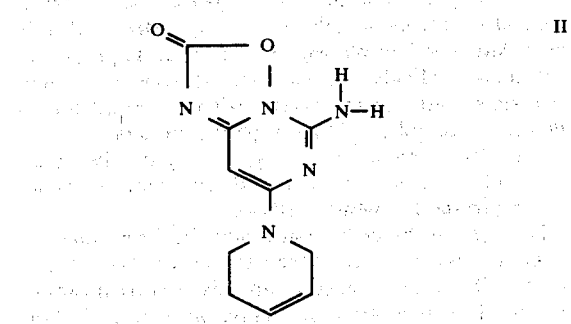

In still another aspect, the invention relates to a process for preparing the compounds of formula I which comprises reacting 5-amino-7-[3,6-dihydro-1(2H)-pyridyl]-2H-[1,2,4]-oxadiazolo[2,3-c]pyrimidin-2-one with an azole derivative of the formula

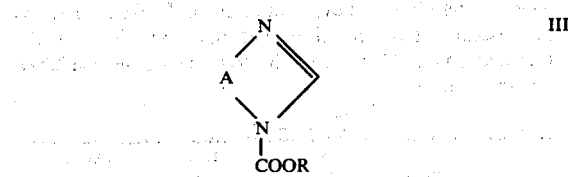

wherein R is alkyl, alkenyl, alkynyl or alkoxyalkyl and A is —CH=CH—,

or —N=CH— whereby the nitrogen is situated in the 2-position.

DETAILED DESCRIPTION OF THE INVENTION

The invention relates to oxadiazolopyrimidine derivatives of the formula

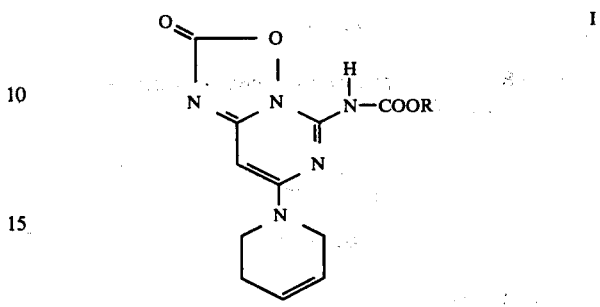

wherein R is alkyl, alkenyl, alkynyl or alkoxyalkyl, as well as pharmaceutically acceptable salts thereof.

The term "alkyl" as used herein alone or in combination, refers to straight-chain and branched-chain, saturated hydrocarbon groups containing 1–8, preferably 1–4, carbon atoms, for example, methyl, ethyl, n-propyl, isopropyl, n-butyl, isobutyl, tert.butyl and the like. The term "alkoxy" denotes alkyl ether groups in which the term "alkyl" has the significance set forth above. The term "alkenyl" denotes straight-chain and branched-chain hydrocarbon groups containing 2–6, preferably 2–3, carbon atoms in which at least one carbon-carbon bond is unsaturated such as allyl, butenyl and the like. The term "alkynyl" denotes straight-chain and branched-chain hydrocarbon groups containing 2–6, preferably 2–3, carbon atoms in which at least one carbon-carbon triple bond is present such as propargyl and the like.

Preferred compounds of formula I are those in which R is alkyl or alkenyl. Especially preferred, are those compounds of formula I in which R is alkyl of 1–4 carbon atoms or alkenyl of 2–3 carbon atoms. Most especially preferred are those compounds of formula I in which R is butyl or allyl, that is, butyl 7-[3,6-dihydro-1(2H)-pyridyl]-2-oxo-2H-[1,2,4]oxadiazolo[2,3-c]pyrimidine-5-carbamate and allyl 7-[3,6-dihydro-1(2H)-pyridyl]-2-oxo-2H-[1,2,4]oxadiazolo[2,3-c]pyrimidine-5-carbamate, respectively.

The compounds of formula I as well as their pharmaceutically acceptable salts can be prepared in accordance with the invention by (a) reacting 5-amino-7-[3,6-dihydro-1(2H)-pyridyl]-2H-[1,2,4]oxidiazolo[2,3-c]pyrimidin-2-one of the formula

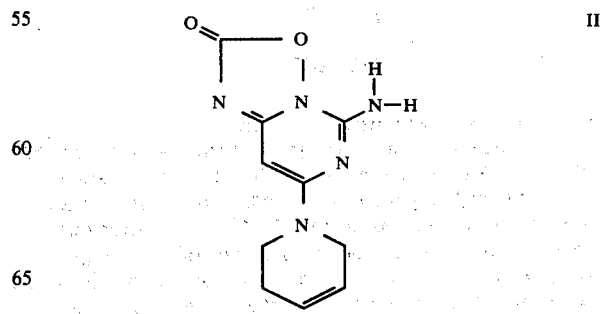

with an azole derivative of the formula

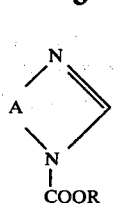

wherein R is as previously described and A is one of the groups —CH=CH—,

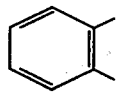

or —N=CH— whereby the nitrogen atom in the latter case is situated in the 2-position, and (b) if desired, converting a compound of formula I obtained into a salt or converting a salt into a pharmaceutically acceptable salt.

The reaction of the compound of formula II with an azole derivative of formula III is carried out according to known methods. Conveniently, the anion of the compound of formula II is reacted with the azole derivative of formula III. The anion of the compound of formula II is advantageously prepared in situ by reaction with a base. Bases, for example, alkali metal hydrides, such as, sodium hydride; alkali metal amides, such as, sodium amide or potassium amide; lithium diisopropylamide; potassium t.butylate and the like, are suitable for this purpose. The reaction is carried out in a solvent which is inert under the reaction conditions and at a temperature in the range of from about −25° C. to room temperature, preferably in the range of from about 0° to 15° C. The solvent can be dimethylformamide, a saturated hydrocarbon, such as, hexane, an aromatic hydrocarbon, such as, benzene, toluene or xylene, an ether, such as, diethyl ether, dioxane or tetrahydrofuran, and the like.

The starting material of formula II is also an object of the invention. It can be prepared, for example, by cyclizing a compound of the formula

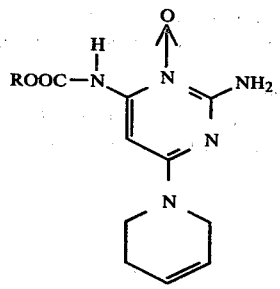

wherein R is as previously described.

The cyclization of a compound of formula IV is carried out in a known manner by heating to a temperature in the range of from about 50° to 200°, preferably in the range of from about 100° to 150° C. The cyclization can be carried out in the absence or presence of a solvent or solvent mixture. If the cyclization is carried out in a solvent or solvent mixture, then the solvent can be an aromatic hydrocarbon such as benzene, toluene or xylene, an ether such as dibutyl ether, dioxane or diethyleneglycol dimethyl ether, dimethylformamide and the like or mixtures thereof. It will be appreciated that there can be used either a solvent whose boiling point lies higher than the cyclization temperature or that there can be used a solvent which boils in the temperature range referred to earlier at its reflux temperature. The cyclization is preferably carried out using dimethylformamide or toluene as the solvent. The cyclization time depends on the temperature at which the cyclization is carried out and is in the range of from about ¼ to 18 hours. If the cyclization is carried out in the preferred temperature range of from about 100° to 150° C., then the cyclization time is in the range of from about ¼ to 12 hours, preferably ½ to 2 hours.

The compounds of formulas III and IV belong to known classes of compounds. Accordingly, they are either previously specifically described or can be obtained in analogy to the preparation of the known compounds.

The compounds of formula I can be converted into salts, for instance by treatment with an inorganic base, for example, an alkali hydroxide, such as sodium hydroxide or potassium hydroxide, or an alkaline earth hydroxide, such as calcium hydroxide. Salts of the compounds of formula I can also be prepared by double-decomposition of a suitable salt. Of the salts of the compounds of formula I, the pharmaceutically usable salts are preferred.

The compounds of formula I as well as their pharmaceutically acceptable salts have long-lasting valuable vasodilating and/or blood pressure-lowering properties and can accordingly be used for the treatment of vascular-conditioned hypertensions or also as vasodilators in the case of peripheral blood supply disorders.

The blood pressure-lowering activity can be determined in conscious, spontaneous hypertensive rats according to the following method:

The systolic blood pressure and the heart rate are measured twice before administration of the test substance. The test substance is administered by means of an oesophageal probe twice daily, morning and afternoon. Both parameters are measured 1, 3, 6 and 24 hours after the administration and the percentage variations to the control values are calculated. The systolic blood pressure is measured indirectly in the tail artery of the rat according to the method of Gerold et al. (Helv. Physiol. Acta 24: 58–69, 1966; Arzneimittelforschung 18: 1285–1287, 1968).

The results obtained are compiled in Table I, in each case maximum percentage deviations from the control values are given. Moreover, the toxicity values are also given in Table I.

TABLE I

| Compound | Dosage mg.kg.$^{-1}$ | Blood Pressure % | Heart rate % | Tox.DL$_{50}$ mg.kg.$^{-1}$ p.o. |
|---|---|---|---|---|
| A | 30 | −14.2 | +10.0 | >4,000 |
|   | 100 | −38.4 | +13.0 | |
| B | 1 | −12.6 | +8.2 | >5,000 |
|   | 3 | −33.4 | +20.0 | |
|   | 10 | −40.0 | +21.2 | |
| C | 10 | −21.8 | +12.7 | >4,000 |
|   | 30 | −27.0 | +14.3 | |
| D | 10 | −31.0 | +9.0 | >5,000 |
| E | 1 | −24.1 | +12.5 | >5,000 |
|   | 3 | −40.9 | +9.4 | |
| F | 10 | −37.3 | +12.7 | >5,000 |
| G | 30 | −27.9 | +12.2 | >5,000 |
| H | 0.3 | −11.3 | +17.7 | >4,000 |

TABLE I-continued

| Compound | Dosage mg.kg.$^{-1}$ | Blood Pressure % | Heart rate % | Tox.DL$_{50}$ mg.kg.$^{-1}$ p.o. |
|---|---|---|---|---|
| | 1 | −19.8 | +12.8 | |
| | 3 | −31.6 | −10.1 | |
| | 10 | −51.3 | −9.1 | |

A = Methyl 7-[3,6-dihydro-1(2H)—pyridyl]-2-oxo-2H—[1,2,4]oxadiazolo[2,3-c]pyrimidine-5-carbamate.
B = Isobutyl 7-[3,6-duhydro-1(2H)—pyridyl]-2-oxo-2H—[1,2,4]oxadiazolo[2,3-c]pyrimidine-5-carbamate.
C = (2-Methoxyethyl) 7-[3,6-dihydro-1(2H)—pyridyl-2-oxo-2H—[1,2,4]oxadiazolo[2,3-c]pyrimidine-5-carbamate.
D = Butyl 7-[3,6-dihydro-1(2H)—pyridyl]-2-oxo-2H—[1,2,4]-oxadiazolo[2,3-c]pyrimidine-5-carbamate.
E = Propyl 7-[3,6-dihydro-1(2H)—pyridyl]-2-oxo-2H—[1,2,4]-oxadiazolo[2,3-c]pyrimidine-5-carbamate.
F = Isopropyl 7-[3,6-dihydro-1(2H)—pyridyl]-2-oxo-2H—[1,2,4]oxadiazolo[2,3-c]pyrimidine-5-carbamate.
G = Propargyl 7-[3,6-dihydro-1(2H)—pyridyl]-2-oxo-2H—[1,2,4]oxadiazolo[2,3-c]pyrimidine-5-carbamate.
H = Allyl 7-[3,6-dihydro-1(2H)—pyridyl]-2-oxo-2H—[1,2,4]-oxadiazolo[2,3-c]pyrimidine-5-carbamate.

The compounds of formula I and their pharmaceutically acceptable salts can be used as medicaments, for example, in the form of pharmaceutical preparations which contain them in association with a pharmaceutical organic or inorganic inert carrier material suitable for enteral or parenteral administration such as, for example, water, gelatine, gum arabic, lactose, starch, magnesium stearate, talc, vegetable oils, polyalkyleneglycols, and the like. The pharmaceutical preparations can be made up in a solid form, for example, as tablets, dragees, suppositories or capsules, or in a liquid form, for example, as solutions, suspensions or emulsions. If necessary, the pharmaceutical preparations can be sterilized and/or can contain adjuvants such as preserving, stabilizing, wetting or emulsifying agents, salts for varying the osmotic pressure or buffers. They can also contain still other therapeutically valuable substances.

The daily dosage in the case of oral administration is in the range of from about 10 to 500 mg and in the case of intravenous administration is in the range of from about 1 to 50 mg. It will, however, be appreciated that these dosages are given by way of example only and can be altered according to the severity of the condition to be treated and according to the judgement of the attending practitioner.

The Examples which follow further illustrate the invention. All temperatures are given in degrees Centigrade, unless otherwise stated: The melting points are not corrected.

EXAMPLE 1

Preparation of methyl 7-[3,6-dihydro-1(2H)-pyridyl]-2-oxo-2H-[1,2,4]oxadiazolo[2,3-c]pyrimidine-5-carbamate 4.30 g of sodium hydride (55–60% dispersion in oil) are washed with hexane and suspended in 150 ml of dimethylformamide under argon. 20.54 g of 5-amino-7-[3,6-dihydro-1(2H)-pyridyl]-2H-[1,2,4]oxadiazolo[2,3-c]pyrimidin-2-one are introduced portionwise within 10 minutes into the stirred, ice-cooled suspension, the temperature is held at 14°. The ice-bath is removed and the mixture is stirred for 30 minutes. Then, a solution of 15.8 g of 1-methoxycarbonyl-imidazole in 50 ml of dimethylformamide is added rapidly and the solution is stirred at 20°–25° for 1 hour. The clear, red-brown solution is poured into 1.2 l of water, the slightly turbid solution is filtered through a Speedex filter bed and treated with 40 ml of glacial acetic acid while stirring. The precipitate is removed by filtration and washed thoroughly with 600 ml of water. The filter cake is triturated in the suction filter with 400 ml of methanol and the solvent removed by suction. After drying (40°, 20 mm Hg), there are obtained 23.37 g (91%) of methyl 7-[3,6-dihydro-1(2H)-pyridyl]-2-oxo-2H-[1,2,4]oxadiazolo[2,3-c]pyrimidine-5-carbamate as a white powder, m.p. 213° (decomposition).

10.00 g of the crude product are dissolved under reflux in 500 ml of methanol and 25 ml of triethylamine and filtered. The warm solution is treated within 30 minutes with 20 ml of glacial acetic acid in 50 ml of methanol and the suspension is stirred at room temperature for an additional 30 minutes. The crystallizate is removed by filtration and washed thoroughly with three 200 ml portions of methanol. After drying (40°, 20 mm Hg), there are obtained 8.99 g of white crystals, m.p. 215° (decomposition).

The 5-amino-7-[3,6-dihydro-1-(2H)-pyridyl]-2H-[1,2,4]oxadiazolo[2,3-c]pyrimidin-2-one used as the starting material can be prepared as follows:

28.8 g of methyl 2-amino-6-[3,6-dihydro-1(2H)-pyridyl]-4-pyrimidinecarbamate-3-oxide are treated with 350 ml of dimethylformamide and the mixture is stirred in an oil-bath at 135° for 30 minutes. The brown solution is evaporated under reduced pressure. The still moist residue is suspended in 350 ml of ether for 1 hour and the crystallizate is removed by filtration and washed with ether. After drying (40°, 20 mm Hg), there are obtained 23.4 g (92.5%) of a light beige, crystalline powder, m.p. 228° (decomposition).

The 1-methoxycarbonyl-imidazole used as the starting material can be prepared as follows:

47.2 g of methyl chloroformate in 60 ml of ether are added dropwise at 10° within 40 minutes to a stirred solution of 34.05 g of imidazole and 52.5 g of triethylamine in 500 ml of acetonitrile. The suspension is stirred at room temperature for 30 minutes. The precipitate is removed by filtration and washed with ether. The filtrate is evaporated under reduced pressure and the residue is taken up in 500 ml of benzene and stirred for 10 minutes. The insoluble material is again removed by filtration and the filtrate is evaporated under reduced pressure, the residual oil slowly solidifying. There are obtained 61.7 g (98%) of a light yellowish solid, m.p. 35°–40°, which can be used without further purification.

EXAMPLE 2

In a manner analogous to that described in Example 1, by reacting 5-amino-7-[3,6-dihydro-1(2H)-pyridyl]-2H-[1,2,4]oxadiazolo[2,3-c]pyrimidin-2-one With 1-isobutyloxycarbonyl-imidazole there is obtained isobutyl 7-[3,6-dihydro-1(2H)-pyridyl]-2-oxo-2H-[1,2,4]oxadiazolo[2,3-c]-pyrimidine-5-carbamate, m.p. 197°–198° (from methylene chloride/methanol/diethyl ether), with 1-(2-methoxyethyl)oxycarbonyl-imidazole there is obtained (2-methoxyethyl) 7-[3,6-dihydro-1(2H)-pyridyl]-2-oxo-2H-[1,2,4]oxadiazolo[2,3-c]pyrimidine-5-carbamate, m.p. 203°–204° (from methylene chloride/methanol/diethyl ether), with 1-butyloxycarbonyl-imidazole there is obtained butyl 7-[3,6-dihydro-1(2H)-pyridyl]-oxo-2H-[1,2,4]oxadiazolo[2,3-c]-pyrimidine-5-carbamate, m.p. 197°–198° (from methylene chloride/methanol/diethyl ether), with 1-ethoxycarbonyl-imidazole there is obtained ethyl 7-[3,6-dihydro-1(2H)-pyridyl]-2-oxo-2H-[1,2,4]oxidiazolo[2,3-c]-pyrimidine-5-carbamate, m.p. 202°–204° (from methylene chloride/methanol/diethyl ether), with 1-propyloxycarbonyl-imidazole there is obtained propyl 7-[3,6-dihydro-1(2H)-pyridyl]-2-oxo-2H-[1,2,4]oxadiazolo[2,3-c]pyrimidine-5-carbamate, m.p. 201°–202° (from methylene chloride/methanol/diethyl ether), with 1-isopropyloxycarbonyl-imidazole there is obtained isopropyl 7-[3,6-dihydro-1(2H)-pyridyl]-2-oxo-2H-[1,2,4]oxadiazolo[2,3-c]pyrimidine-5-carbamate, m.p. 186°–187° (from methylene chloride/methanol/diethyl ether), with 1-propargyloxycarbonyl-imidazole there is obtained propargyl 7-[3,6-dihydro-1(2H)-pyridyl]-2-oxo-2H-[1,2,4]oxadiazolo[2,3-c]pyrimidine-5-carbamate, m.p. 211°–213° (from methylene chloride/methanol/diethyl ether) and with 1-allyloxycarbonyl-imidazole there is obtained allyl 7-[3,6-dihydro-1(2H)-pyridyl]-2-oxo-2H-[1,2,4]oxadiazolo[2,3-c]pyrimidine-5-carbamate, m.p. 207°–209° (from methylene chloride/methanol/diethyl ether).

The aforementioned imidazole derivatives used as the starting materials are prepared in a manner analogous to that described in the last paragraph of Example 1 by reacting imidazole with a corresponding chloroformic acid ester. Since there derivatives are not crystalline at room temperature, they are characterized with the aid of spectroscopic methods.

EXAMPLE 3

Preparation of methyl 7-[3,6-dihydro-1(2H)-pyridyl]-2-oxo-2H-[1,2,4]oxadiazolo[2,3-c]pyrimidine-5-carbamate 1.2 g of sodium hydride are added portionwise to a solution, cooled to 15°, of 4.66 g of 5-amino-7-[3,6-dihydro-1(2H)-pyridyl]-2H-[1,2,4]oxadiazolo[2,3-c]pyrimidin-2-one in 200 ml of dimethylformamide. The mixture is stirred vigorously at room temperature for 30 minutes. Thereafter, 5.28 g of 1-methoxycarbonylbenzimidazole in 50 ml of dimethylformamide are added thereto. After 2 hours, the mixture is treated with ice-cold water and adjusted to pH 5 with glacial acetic acid. The precipitate which results is recrystallized from methylene chloride/methanol, and there is obtained methyl 7-[3,6-dihydro-1(2H)-pyridyl]-2-oxo-2H-[1,2,4]oxadiazolo[2,3-c]pyrimidine-5-carbamate, m.p. 212°–214°

The 1-methoxycarbonyl-benzimidazole used as the starting material can be prepared as follows:

16.72 ml of triethylamine are added dropwise to a solution of 11.8 g of benzimidazole in acetonitrile. There is added thereto at 10° a solution of 7.68 ml of methyl chloroformate in 30 ml of ether. The precipitate is removed by filtration and the solution is evaporated under reduced pressure. The thus-obtained 1-methoxycarbonyl-benzimidazole is used without further purification.

EXAMPLE 4

Preparation of sodium salt of methyl 7-[3,6-dihydro-1(2H)-pyridyl]-2-oxo-2H-[1,2,4]-oxadiazolo[2,3-c]pyrimidine-5-carbamate 13 g of methyl 7-[3,6-dihydro-1(2H)-pyridyl]-2-oxo-2H-[1,2,4]oxadiazolo[2,3-c]pyrimidine-5-carbamate are stirred in 100 ml of water and treated slowly with 44.7 ml of 1 N aqueous sodium hydroxide (1.001 mol equivalents), the pH change is followed until the pH is stable. As soon as the pH value is stable, the solution obtained is filtered, freeze-dried and lyophilized. After repeated drying at 50° in a high vacuum, there are obtained 13.5 g of the sodium salt of methyl 7-[3,6-dihydro-1(2H)-pyridyl]-2-oxo-2H-[1,2,4]oxadiazolo[2,3-c]pyrimidine-5-carbamate in the form of a fine white powder of melting point 192°–198°.

In an analogous manner, from 33 g of butyl 7-[3,6-dihydro-1(2H)-pyridyl]2-oxo-2H-[1,2,4]oxidiazolo[2,3-c]pyrimidine-5-carbamate and 1.001 mol equivalents of 1 N aqueous sodium hydroxide there is obtained the corresponding sodium salt having a melting point of 158°–169°.

EXAMPLE A

Tablets containing the following ingredients are prepared:

| | | |
|---|---|---|
| I | Butyl 7-[3,6-dihydro-1(2H)-pyridyl]-2-oxo-2H-[1,2,4]oxadiazolo[2,3-c]-pyrimidine-5-carbamate (micronized) | 20.0 mg |
| | Lactose (powdered) | 40.0 mg |
| | Maize starch (white) | 24.9 |
| II | Dioctyl sodium sulfosuccinate | 0.1 mg |
| | Maize starch (white) | 5.0 mg |
| | Water | q.s. |
| III | Maize starch (white) | 6.0 mg |
| IV | Talc | 3.0 mg |
| | Magnesium stearate | 1.0 mg |
| | | 100.0 mg |

The ingredients of group I are sieved and mixed. This mixture is moistened with the maize starch paste comprising group II and kneaded. The moist mass is granulated, dried and made into a suitable granular size. Group III is admixed. The resulting mixture is mixed with group IV for an additional short time. The ready-to-press mixture is pressed into tablets weighing 100 mg, having a diameter of 7 mm and having a break-bar.

EXAMPLE B

Tablets containing the following ingredients are prepared:

| | | |
|---|---|---|
| I | Butyl 7-[3,6-dihydro-1(2H)-pyridyl]-2-oxo-2H-[1,2,4]oxadiazolo[2,3-c]-pyrimidine-5-carbamate (micronized) | 200.0 mg |
| | Lactose (powdered) | 42.9 mg |
| | Maize starch (white) | 50.0 mg |
| II | Dioctyl sodium sulfosuccinate | 0.1 mg |
| | Maize starch (white) | 20.0 mg |
| | Water | q.s |
| III | Maize starch (white) | 30.0 mg |
| IV | Talc | 3.5 mg |
| | Magnesium stearate | 3.5 mg |
| | | 350.0 mg |

The ingredients of group I are sieved and mixed. This mixture is moistened with the maize starch paste comprising group II and kneaded. The moist mass is granulated, dried and made into a suitable granular size. Group III is admixed. The resulting mixture is mixed with group IV for an additional short time. The ready-to-press mixture is pressed to tablets weighing 350 mg, having a diameter of 11 mm and having a break-bar.

EXAMPLE C

Capsules containing the following ingredients are prepared:

| | | |
|---|---|---|
| I | Butyl 7-[3,6-dihydro-1(2H)—pyridyl]-2-oxo-2H—[1,2,4]oxadiazolo[2,3-c]-pyrimidine-5-carbamate (micronized) | 20.0 mg |
| | Lactose (powdered) | 5.0 mg |
| II | Maize starch | |
| | Water | q.s. |
| III | Lactose (crystalline) | 50.0 mg |
| | Maize starch | 15.0 mg |
| IV | Talc | 10.0 mg |
| | Magnesium stearate | 2.0 mg |
| | | 150.0 mg |

The ingredients of group I are sieved and mixed. This mixture is moistened with the maize starch paste comprising group II and kneaded. The moist mass is granulated, dried and made into a suitable granular size. Group III is admixed. The resulting mixture is mixed with group IV for an additional short time. The capsule mixture is filled into capsules (size 2) each containing 150 mg.

EXAMPLE D

An aqueous drop suspension containing the following ingredients is prepared:

| | 10 mg per 1 ml |
|---|---|
| Butyl 7-[3,6-dihydro-1(2H)—pyridyl]-2-oxo-2H—[1,2,4]oxadiazolo[2,3-c]-pyrimidine-5-carbamate (micronized) | 0.1 g |
| sodium benzoate | 0.035 g |
| Saccharin sodium | 0.015 g |
| Acrylic acid polymerizate | 0.1–1.0 g |
| Saccharose | 3.5 g |
| Citric acid | 0.025 g |
| Polyoxyethylene stearate | 0.002–0.1 g |
| Sodium hydroxide | q.s. |
| Flavor | q.s. |
| Food coloring | q.s. |
| Deionized water | ad 10.0 ml |

EXAMPLE E

Tablets, capsules and injection preparations can be prepared according to the procedures described in Examples A–D using the following, similarily preferred, compounds and their pharmaceutical acceptable salts:
Methyl 7-[3,6-dihydro-1(2H)-pyridyl]-2-oxo-2H-[1,2,4]oxadiazolo[2,3-c]pyrimidine-5-carbamate;
ethyl 7-[3,6-dihydro-1(2H)-pyridyl]-2-oxo-2H-[1,2,4]oxadiazolo[2,3-c]pyrimidine-5-carbamate;
propyl 7-[3,6-dihydro-1(2H)-pyridyl]-2-oxo-2H-[1,2,4]oxadiazolo[2,3-c]pyrimidine-5-carbamate;
isopropyl 7-[3,6-dihydro-1(2H)-pyridyl]-2-oxo-2H-[1,2,4]oxadiazolo[2,3-c]pyrimidine-5-carbamate;
isobutyl 7-[3,6-dihydro-1(2H)-pyridyl]-2-oxo-2H-[1,2,4]oxadiazolo[2,3-c]pyrimidine-5-carbamate; and
allyl 7-[3,6-dihydro-1(2H)-pyridyl]2-oxo-2H-[1,2,4]oxadiazolo[2,3-c]pyrimidine-5-carbamate.

We claim:
1. A compound of the formula

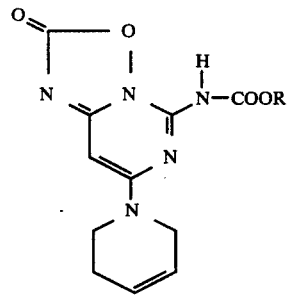

wherein R is alkyl of 1–8 carbon atoms, alkenyl, of 2–6 carbon atoms, alkynyl of 2–6 carbon atoms, or ($C_{1-8}$)alkoxy-( $C_{1-8}$)alkyl, or a pharmaceutically acceptable salt thereof.

2. A compound in accordance with claim 1, wherein R is alkyl or alkoxyalkyl.

3. A compound in accordance with claim 1, wherein R is alkyl or alkenyl.

4. A compound in accordance with claim 3, wherein R is alkyl of 1–4 carbon atoms or alkenyl of 2–3 carbon atoms.

5. The compound in accordance with claim 1, methyl 7-[3,6-dihydro-1(2H)-pyridyl]-2-oxo-2H-[1,2,4]oxadiazolo[2,3-c]pyrimidine-5-carbamate.

6. The compound in accordance with claim 1, ethyl 7-[3,6-dihydro-1(2H)-pyridyl]-2-oxo-2H-[1,2,4]oxadiazolo[2,3-c]pyrimidine-5-carbamate.

7. The compound in accordance with claim 1, isobutyl 7-[3,6-dihydro-1(2H)-pyridyl]-2-oxo-2H-[1,2,4]oxadiazolo[2,3-c]pyrimidine-5-carbamate.

8. The compound in accordance with claim 1, butyl 7-[3,6-dihydro-1(2H)-pyridyl]-2-oxo-2H-[1,2,4]oxadiazolo[2,3-c]pyrimidine-5-carbamate.

9. The compound in accordance with claim 1, propyl 7-[3,6-dihydro-1(2H)-pyridyl]-2-oxo-2H-[1,2,4]oxadiazolo[2,3-c]pyrimidine-5-carbamate.

10. The compound in accordance with claim 1, isopropyl 7-[3,6-dihydro-1(2H)-pyridyl]-2-oxo-2H-[1,2,4]oxadiazolo[2,3-c]pyrimidine-5-carbamate.

11. The compound in accordance with claim 1, allyl 7-[3,6-dihydro-1(2H)-pyridyl]-2-oxo-2H-[1,2,4]oxadiazolo[2,3-c]pyrimidine-5-carbamate.

12. A pharmaceutical composition comprising a compound of the formula

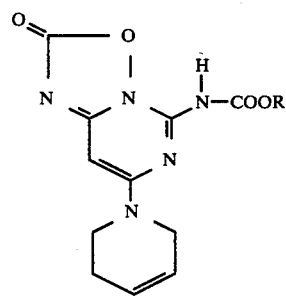

wherein R is alkyl of 1–8 carbon atoms, alkenyl, of 2–6 carbon atoms, alkynyl of 2–6 carbon atoms, or ($C_{1-8}$)alkoxy-( $C_{1-8}$)alkyl, or a pharmaceutically acceptable salt thereof and an inert carrier material.

* * * * *